US00PP20103P2

(12) United States Plant Patent
Hofmann

(10) Patent No.: US PP20,103 P2
(45) Date of Patent: Jun. 16, 2009

(54) **NEW GUINEA *IMPATIENS* PLANT NAMED 'FISNICS REDDIE'**

(50) Latin Name: *Impatiens hawkeri*
Varietal Denomination: Fisnics Reddie

(75) Inventor: Birgit Christa Hofmann, Bendorf (DE)

(73) Assignee: Syngenta Participations AG (CH)

( * ) Notice: Subject to any disclaimer, the term of this patent is extended or adjusted under 35 U.S.C. 154(b) by 69 days.

(21) Appl. No.: 12/077,693

(22) Filed: Mar. 20, 2008

(51) Int. Cl.
*A01H 5/00* (2006.01)

(52) U.S. Cl. ..... Plt./318.7
(58) Field of Classification Search ..... Plt./318.7
See application file for complete search history.

*Primary Examiner*—Annette H Para
(74) *Attorney, Agent, or Firm*—S. Matthew Edwards

(57) ABSTRACT

A new New Guinea *Impatiens* plant particularly distinguished by having large, intense red-colored flowers held well above the foliage, deep green, glossy foliage, a medium-sized, mounded, relatively tight plant habit, and an early to medium flowering response, is described.

1 Drawing Sheet

Genus and species:
*Impatiens hawkeri* W. Bull.
Variety denomination: 'Fisnics Reddie'.

BACKGROUND OF THE NEW PLANT

The present invention comprises a new and distinct cultivar of New Guinea *Impatiens* botanically known as *Impatiens hawkeri* W. Bull, and hereinafter referred to by the cultivar name 'Fisnics Reddie'. The new cultivar originated from a hybridization made in the year 2003 in Hillscheid, Germany. The female parent was the proprietary *Impatiens* plant 'K03-2482-1' (unpatented), while the male parent was the proprietary *Impatiens* plant 'K02-0128-1' (unpatented). The seeds produced by the hybridization were sown in a greenhouse in Moncarapacho, Portugal in the fall of 2003. A single plant selection was chosen for further evaluation and for asexual propagation in the spring of 2004 in Moncarapacho, Portugal.

The new cultivar was created in 2003 in Hillscheid, Germany and has been asexually reproduced repeatedly by vegetative cuttings and tissue culture in Moncarapacho, Portugal and Hillscheid, Germany over a three-year period. 'Fisnics Reddie' has not been observed under all possible environmental conditions. The phenotype may vary significantly with variations in environment such as temperature, light intensity and day length, without, however, any variation in genotype. The present invention has been found to retain its distinctive characteristics through successive asexual propagations.

Plant Breeder's Rights for this cultivar were applied for in Canada on Mar. 30, 2007, and in Switzerland, on May 23, 2007. 'Fisnics Reddie' has not been made publicly available more than one year prior to filing of this application.

SUMMARY OF THE INVENTION

The following are the most outstanding and distinguishing characteristics of this new cultivar when grown under normal horticultural practices in Hillscheid, Germany, and in Langley, British Columbia, Canada.

1. Intense red flower color;
2. Large flowers held well above the foliage;

3. Deep green, glossy foliage;
4. Medium sized, mounded, relatively tight plant habit;
5. Early to medium flowering response; and
6. Suitable for containers as well as bedding plants.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13 to 15 weeks old, grown in a greenhouse in Hillscheid, Germany, in the spring of 2007.

DESCRIPTION OF THE NEW CULTIVAR

The following detailed descriptions set forth the distinctive characteristics of 'Fisnics Reddie'. The data which defines these characteristics were collected from asexual reproductions carried out in Hillscheid, Germany. The plant history was taken on 10- to 12-week-old plants which were planted as rooted cuttings in 12-cm pots in late February 2007, and then grown in a greenhouse at a minimum temperature of 16° C. Color readings were taken under natural light in the greenhouse. Color references are primarily to the RHS Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens*.

Parentage:
*Female parent.*—'K03-2482-1' a proprietary red-flowered New Guinea *Impatiens* plant (unpatented).
*Male parent.*—'K02-0128-1' a proprietary red-flowered New Guinea *Impatiens* plant (unpatented).

Growth:

*Growth and branching habit.*—Medium size, round, bushy, and well-branched; the growth is indeterminate, though weak after the beginning of flowering.

*Height.*—12.7 cm.

*Width.*—32.7 cm.

*Propagation.*—Terminal tips for cuttings.

*Time to produce a finished flowering plant.*—9 to 10 weeks for a 12-cm pot.

*Time to initiate and develop roots.*—About 18 days at 22° C.

*Outdoor plant performance.*—Suitable for use in containers as well as in flower beds.

Branches:

*Average number.*—7.2.

*Length of branches.*—About 10 cm to 14 cm.

*Internode length.*—1.5 cm to 2.0 cm.

*Diameter of branches.*—0.5 cm to 0.9 cm.

*Stem color.*—RHS 185A (purple) with RHS 187A (deep purple) at tips.

Leaves:

*Arrangement.*—Primarily in whorls.

*Size.*—Length: 13.9 cm. Width: 4.8 cm.

*Shape.*—Elliptic or narrow-elliptic.

*Margin.*—Slightly serrate, ciliate.

*Apex.*—Acuminate.

*Base.*—Acute.

*Color* (*Both immature and mature leaves*).—Upper surface: Between RHS 137A and RHS 139A. Lower surface: Near RHS 139C.

*Texture.*—Upper surface: Glabrous, smooth to slightly rippled, glossy. Lower surface: Smooth with protruding veins.

*Venation color.*—Upper surface: RHS 53C (light red) towards base, fading towards tip. Lower surface: RHS 53D or RHS 181B (pink).

*Variegation.*—None.

*Petioles.*—Length: 3.1 cm. Diameter: 0.3 cm. Color: Upper surface: RHS 53A to RHS 53B. Lower surface: RHS 181A. Texture: Glabrous.

Flower buds:

*Shape.*—Ovoid.

*Size.*—Length: 2.2 cm. Diameter: 1.5 cm.

*Color.*—Near RHS 43A (Red).

Inflorescence:

*Blooming habit.*—9 weeks after planting of rooted cuttings.

*Inflorescence type.*—Flowers appear solitary in the leaf axiles of the upper nodes of the stems.

*Number of flowers per node.*—About 5 to 8, in various stages of development.

*Flowering season.*—Mainly from March to October, depending on light intensity.

*Lastingness of individual blooms.*—Up to about 10 days (greenhouse, 18° C., in spring).

*Peduncle.*—Color: RHS 53A or RHS 185A (deep purple red). Size: Length: 4.7 cm. Diameter: 0.2 cm. Texture: Glabrous, flexible.

Flowers:

*Form of corolla.*—Single with 5 petals.

*Shape of corolla.*—Nearly round to somewhat zygomorphic, with the petals partly overlapping, almost flat.

*Corolla size.*—(usually diminishes a little during the summer). Length: 8.1 cm. Width: 7.9 cm. Depth: 1.0 cm to 1.2 cm.

*Fragrance.*—None.

Petals:

*Shape.*—Cordate, weakly to distinctly lobed at the top, occasionally a little wavy.

*Apex.*—Emarginate.

*Base.*—Attenuate.

*Margin.*—Entire.

*Petal size.*—Upper petal: Length: 3.3 cm to 3.5 cm. Width: 5.2 cm to 5.3 cm. Lateral petal: Length: 3.3 cm to 3.5 cm. Width: 3.7 cm to 3.8 cm. Lower petal: Length: 3.6 cm to 3.8 cm. Width: 4.4 cm to 4.6 cm.

*Color.*—General color description: Medium red, brilliant. Upper surface of petals: Immature: Between RHS 46A and RHS 46B. Mature: Uniform RHS 46B. Lower surface: Immature: Between RHS 46A and RHS 46B. Mature: RHS 43B. Eye Zone: No distinct eye zone.

*Petal texture.*—Upper surface: Satiny. Lower surface: Smooth, glabrous.

*Aspect.*—Horizontally, somewhat parallel to the foliage canopy, occasionally somewhat wavy or slightly reflexed.

Calyx:

*General.*—3 to 5 sepals with a large sepal transformed into the spur, two lateral sepals, and the fourth and fifth sepals fused, keel-like with the underside of the banner petal; large sepal bearing the spur.

*Spur.*—Shape: Downwardly curved. Color: RHS 53A to RHS 53B (Red to red-purple). Size: Length: 5.8 cm. Diameter: 0.3 cm at the flower end to 0.5 cm at the tip. Large sepal: Shape: Ovate. Length: 2.1 cm. Width: 1.6 cm. Apex: Cuspidate. Base: Rounded. Color (both surfaces): Near RHS 54C (pink). Lateral sepals: Shape: Elliptic. Length: 1.4 cm. Width: 0.5 cm. Apex: Acuminate to cuspidate. Base: Rounded. Margin: Entire. Color: RHS 174A to 176D (brownish) semi-transparent.

Reproductive organs:

*Stamens.*—Number: 5 fused. Length: 0.5 cm to 0.6 cm. Stamen color (upper surface color): RHS 43B. Anthers: Fused, hooded. Pollen color: RHS 8D (whitish-yellow).

Pistils.—Style and stigma: 5, very short, RHS 150D (pale yellow). Ovary length: 5 cm to 6 cm. Ovary color: RHS 143A (green).

Fruit and seed set: No seed set observed.

Disease and insect resistance: No particular resistance or susceptibility has been observed.

COMPARISON WITH PARENTAL AND COMMERCIAL CULTIVARS

'Fisnics Reddie' differs from the female parent 'K03-2482-1' (unpatented) by having deep red flowers without any distinct bluish hue, while the parent has cherry-red flowers. Additionally flowers of 'Fisnics Reddie' are borne more above the foliage, while those of 'K03-2482-1' are close to the foliage.

'Fisnics Reddie' differs from the male parent 'K02-0128-1' (unpatented), by having earlier flowering, a similar main flower color but with less fading at the margins, and a tighter plant habit.

'Fisnics Reddie' differs from cultivar 'BFP-523 Deep Red' marketed under the Celebration trademark. (U.S. Plant Pat. No. 9,521) by having red flowers without any bluish hue, flatter, less cup-shaped flowers, deeper green foliage, and mainly purple stems, while stems of 'Celebration Deep Red' are partly green, partly brownish-red.

'Fisnics Reddie' differs from the co-applied variety 'Fisnics Reora' (U.S. Plant patent application Ser. No. 12/077,983) by having smaller flowers and a taller plant habit than 'Fisnics Reora'.

I claim:

1. A new and distinct cultivar of New Guinea *Impatiens* plant as shown and described herein.

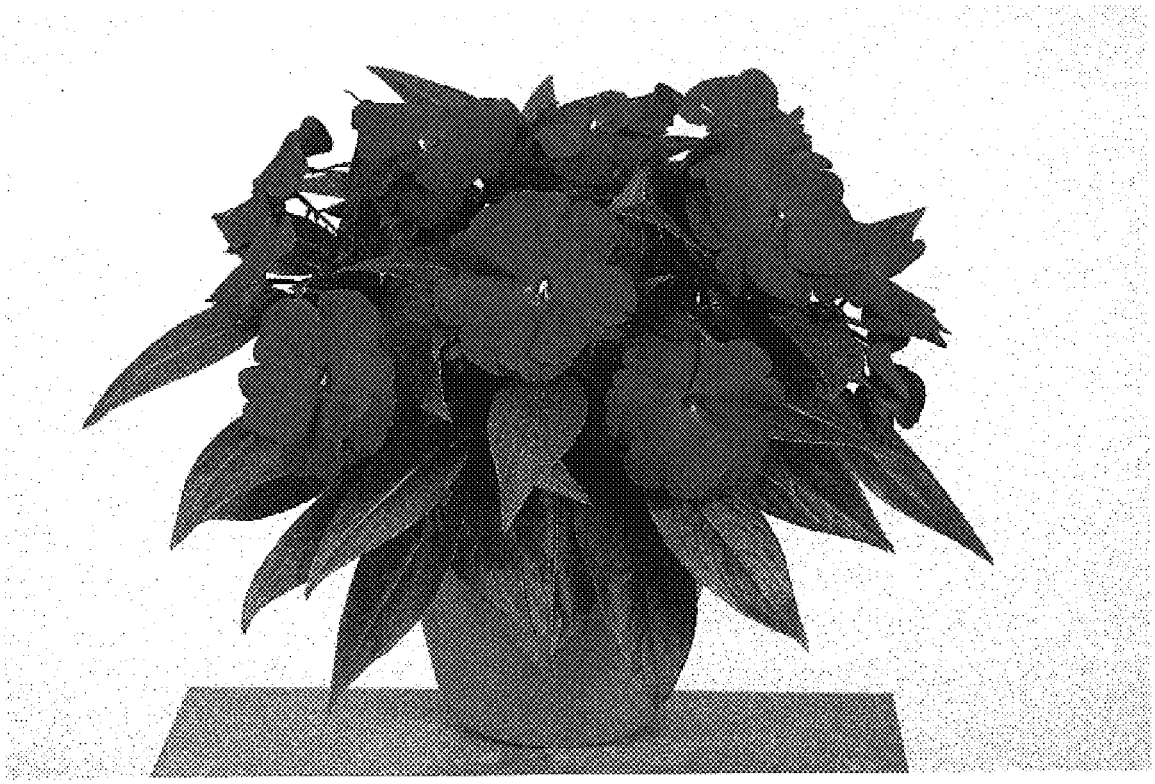

* * * * *